United States Patent
Gartside et al.

(10) Patent No.: US 6,759,562 B2
(45) Date of Patent: Jul. 6, 2004

(54) OLEFIN PLANT RECOVERY SYSTEM EMPLOYING A COMBINATION OF CATALYTIC DISTILLATION AND FIXED BED CATALYTIC STEPS

(75) Inventors: Robert J. Gartside, Summit, NJ (US); Robert I. Haines, West Milford, NJ (US); Thomas Skourlis, Basking Ridge, NJ (US); Charles Sumner, Livingston, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 0 days.

(21) Appl. No.: 10/202,702

(22) Filed: Jul. 24, 2002

(65) Prior Publication Data

US 2004/0019245 A1 Jan. 29, 2004

(51) Int. Cl.$^7$ .............................. C07C 5/05; C07C 5/03
(52) U.S. Cl. ...................... 585/265; 585/258; 585/259; 585/262
(58) Field of Search ................................ 585/265, 258, 585/254, 262

(56) References Cited

FOREIGN PATENT DOCUMENTS

WO      WO 95/15934     * 6/1995

* cited by examiner

Primary Examiner—Thuan D. Dang
(74) Attorney, Agent, or Firm—Alix, Yale & Ristas, LLP

(57) ABSTRACT

Presented is an improvement to a previous invention involving the catalytic hydrogenation of the $C_2$ to $C_5$ and heavier acetylenes and dienes in a thermally cracked feed stream without significantly hydrogenating the $C_2$ and $C_3$ olefins. The improvement involves the use of a fixed bed hydrogenation reactor system in combination with a modified version of the catalytic distillation unit used in the prior art. The modification to the catalytic distillation unit involves improvement of the liquid recycle scheme. The fixed bed reactors combined with the modified catalytic distillation allows for 100% conversion of acetylene and helps to maintain high conversion of the other dienes and acetylenes with no ethylene or propylene conversion under a variety of conditions. These condition variations include but are not limited to the feed diene and acetylene composition, the mol % carbon monoxide in the feed, and catalyst deactivation. With catalytic distillation alone, complete conversion of the acetylene as stated above can not be achieved without ethylene loss, nor would satisfactory operation and control be possible under the variety of conditions experienced during a commercial operation.

29 Claims, 7 Drawing Sheets

OLEFIN PLANT RECOVERY SYSTEM EMPLOYING A COMBINATION OF CATALYTIC DISTILLATION AND FIXED BED CATALYTIC STEPS

BACKGROUND OF THE INVENTION

The present invention relates to a method for the production of olefins and particularly to processing the cracking heater effluent to more effectively recover the product and process the by-products.

In the production of ethylene and propylene through the pyrolysis of a variety of feedstocks, several byproducts and unsaturated diolefins and acetylenes are created. The net effluent from the pyrolysis heaters, typically referred to as charge gas, requires processing for the separation of the byproducts and removal of the diolefins and acetylenes from the primary olefin products. Removal of the $C_2$ and heavier diolefins and acetylenics from the cracked gas is handled through a combination of separation via distillation and reaction via hydrogenation. Specifically for acetylene, separation alone would result in excessive loss of the ethylene product since acetylene and ethylene have very similar relative volatility. Currently, the distillation and hydrogenation take place in several distinct process steps that are designed to separate and hydrogenate the $C_2$, $C_3$, and $C_4$ compounds independently. Separation of the different hydrocarbons before hydrogenation is currently required for achieving better control over the hydrogenation, prolonging catalyst life, and enhancing performance.

One disadvantage of this widely practiced conventional technology is the large energy consumption necessary to generate the high pressures and cryogenic temperatures required to separate first the hydrogen from the cracked gas and then subsequently the molecules of higher carbon number. Additionally, the hydrogenation steps for each of the hydrocarbon groups require an independent reactor system consisting of several pieces of equipment driving up the capital investment and complexity of the plant.

The invention outlined in the previous U.S. Pat. No. 5,679,241 proposes the one-step conversion of all $C_2$ to $C_5$ and heavier acetylenes and dienes without hydrogenation of the $C_2$ or $C_3$ olefins. It is claimed that this is possible with one catalytic distillation unit capable of treating the hot, relatively low pressure charge gas before excessive compression and cryogenic cooling is performed. In addition, if desired, this same one step process claims to be capable of hydrogenating the $C_4$ olefins to paraffins again without the loss of $C_2$ or $C_3$ olefins. The patent relates to a system that is described as being capable of removing 70% and more of the hydrogen in the cracked gas prior to the required cryogenic separation by the hydrogenation of the $C_2$ to $C_4$ acetylenes and dienes and the $C_4$ and heavier olefins to paraffins. Removal of 70% or more of the hydrogen improves the economics through a significant lowering of the energy requirements for separation of the $C_2$ and heavier components. By reducing the hydrogen partial pressure, separation is achieved at lower pressures and with reduced refrigeration. However, it has been shown that such extensive hydrogenation in a single step system cannot occur without substantial loss of ethylene and propylene to paraffins by hydrogenation.

The process as described in U.S. Pat. No. 5,679,241 has significant limitations. First, in the operation of an ethylene plant, the $C_2$ acetylene specifically must be removed via hydrogenation since its removal via distillation is extremely difficult requiring extensive equipment and energy costs. Since acetylene is a polymerization catalyst poison, it must be removed to low levels, often less than 1–2 ppm. The ability to hydrogenate all of the $C_2$ acetylene to that level in a single catalytic distillation column while observing no ethylene loss or preferably a gain was not possible at reasonable catalyst volumes and commercially viable operating conditions. Second, maintaining performance of the process during either a variation in carbon monoxide flow, which impacts catalyst activity, and/or the concentration of diene/acetylene in the feed was hard to manage and would prove difficult to achieve at commercial scale. Third, methods of handling eventual catalyst deactivation were limited. Since these units must operate for long periods of time between shutdowns, the only options were excessive catalyst or separate catalyst zones in the reaction column that can be isolated and the catalyst replaced while the other section remains in operation. When using larger catalyst volumes, it is known that it is necessary to operate at lower temperatures to avoid over-reaction while the catalyst is still active. This negatively impacts the economics by requiring some refrigeration to control operation at lower temperature and/or excessive recycles of cool liquid within the column. Specifically pilot testing has shown that:

a. When the single catalytic distillation column was operated to remove greater: than 95% of the $C_2$ acetylene, the concurrent ethylene loss was above 1% by weight. This is undesirable economically.

b. When operating a single catalytic distillation column, if the hydrogenation of $C_4$ olefins is greater than 20%, significant ethylene loss is to be expected with presently available catalysts.

c. In order to achieve minimal ethylene and propylene losses while operating a single catalytic distillation column and maintaining extremely high conversions and hydrogen removals, the design required excessive catalyst as evidenced by low productivity and operation at cooler temperatures requiring refrigeration.

d. A significant variation in catalyst activity will occur with variations in the carbon monoxide in the feed. Such variations if seen in a single step process, will result in loss of acetylene removal efficiency and subsequent products which do not meet specification. This impact on performance due to the loss of catalytic activity via CO poisoning is equivalent to the impact on performance due to catalyst aging.

e. A significant variation in feedstock to the ethylene cracking heaters will result in substantial changes in both the acetylenes and dienes as well as the hydrogen flow. As the ratio of hydrogen to reactants changes, a single step process has limited ability to follow such changes. The results will be either a breakthrough of acetylene leading to offspec ethylene product or a high loss of valuable ethylene and propylene due to over-reaction, unless the system has substantial and expensive overdesign which could be utilized to surmount these process changes.

SUMMARY OF THE INVENTION

The present invention relates to an improved process for the processing of the charge gas effluent from the pyrolysis of a variety of feedstocks. The primary objective is still to remove a significant fraction of the hydrogen in the effluent by hydrogenating the $C_2$ to $C_5$ diolefins and acetylenes in the feed while achieving essentially total hydrogenation of the $C_2$ acetylene without significant hydrogenation of the ethylene and propylene. In the improved process, this is achieved even with disturbances in the carbon monoxide concentration, varying diene and acetylenic feed concentrations and catalyst deactivation as well as other foreseeable processing upsets. The invention relates to catalytic distillation with improved liquid recycle in combination with fixed bed hydrogenation reactor systems. Specifically, the operating conditions of the catalytic distillation are maintained or adjusted to obtain the maximum hydrogenation of the acetylenes and dienes but without any loss of ethylene and propylene and preferably with an ethylene gain by $C_2$ acetylene hydrogenation. Maintaining a stable high conversion of all of the $C_2$ to $C_5$ acetylenes and dienes with 100% conversion of the $C_2$ acetylene (still without hydrogenating the ethylene and propylene) under varying process conditions is made possible by the fixed bed hydrogenation system in which the remaining $C_2$ acetylene is completely hydrogenated again without significant ethylene or propylene hydrogenation.

DESCRIPTION OF THE PREFERRED EMBODIMENTS

Figure 1:
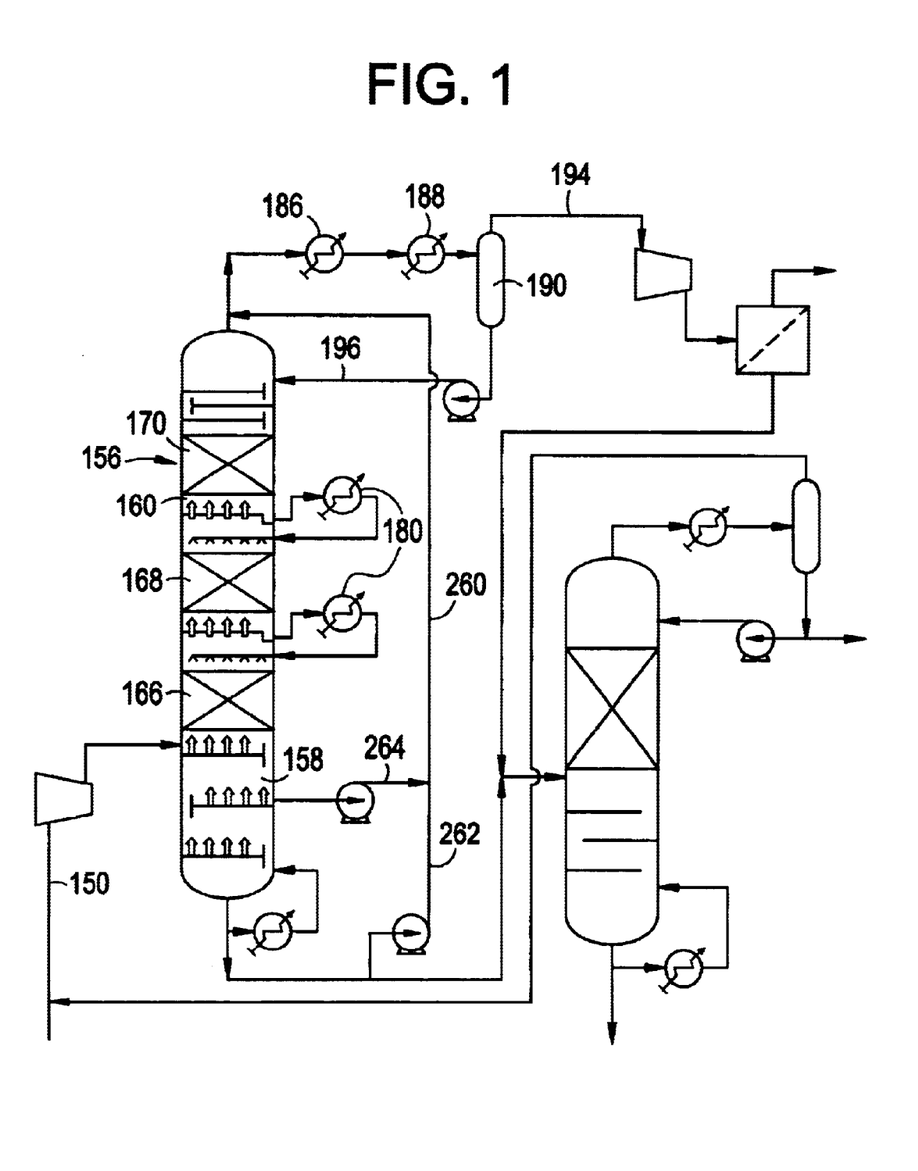
FIG. 1 is a flow diagram of the prior art involving catalytic distillation alone with the bottoms recirculation for temperature control.

For a better understanding of the present invention, the prior art as represented by the process disclosed in U.S. Pat. No. 5,679,241 will be briefly described. FIG. 1 of the drawings of the present invention is essentially a copy of a drawing from that prior patent simplified to identify only those features relevant to the present invention. The charge gas 150 is compressed and fed to the catalytic distillation column 156. This column, as in the present invention, simultaneously carries out a catalytic reaction and distillation. The column has a stripping section 158 below the feed and a rectifying/reaction section 160 above the feed containing the catalyst beds 166, 168 and 170. Descending liquid is withdrawn as sidestreams through the intercondensers 180 and reinjected back into the column over the next lower catalyst bed. A portion of the heat of reaction is removed by these intercondensers. A liquid recycle stream 260 from the stripping section is recycled to the column overhead. This recycle 260 may be a portion 262 of the bottoms and/or a portion 264 from within the stripping section.

The overhead from column 156 passes into condensers 186 and 188 and the partially condensed stream enters separation vessel 190. The product $C_2$ to $C_5$ vapor overhead 194, containing ethylene and propylene, then passes out to subsequent separation while the condensed hydrocarbons are utilized as reflux 196 for the column. Since the objective of the invention is to completely remove the acetylene impurities from ethylene with no loss of the ethylene entering the column, this must be accomplished in this single step operation (one catalytic distillation column). The overhead vapor stream passes into additional fractionation (not shown) where the individual carbon number fractions are isolated.

The hydrogenation in catalytic distillation column 156 occurs in the liquid phase. The column is operated such that liquid phase composition is primarily $C_5$ components. This minimizes the liquid phase concentration of the ethylene and propylene and thus minimizes their reaction. However, the concentration of these two valuable olefins in the liquid will not be zero. The $C_2$ acetylenes and the $C_3$ acetylenes and diolefins are more reactive than their olefin counterpart. In the liquid phase, these are preferentially reacted to ethylene and propylene respectively. However, as the reaction moves to completion close to the desired 100% $C_2$ acetylene conversion, there is no longer a significant concentration of more reactive $C_2$ acetylene present in the liquid phase. Under these conditions, ethylene can react to form ethane (paraffin). This is the point where ethylene loss occurs.

There are several options for reducing the reactivity in the catalyst beds of this upper portion of the catalytic distillation column. One option is to reduce the temperature. Reducing the temperature in one section is difficult in a single column concept because the distillation temperature is primarily controlled by the column pressure. To do this, a second column operating at a lower pressure would be required. A second option is to utilize a different catalyst in this upper section. This catalyst would be designed to more selectively hydrogenate acetylenes and diolefins. Both of these options would however require higher volumes of catalyst within the column and thus increase the column size and cost. A third option is to utilize an intercooler as shown on the prior art.

Figure 2:
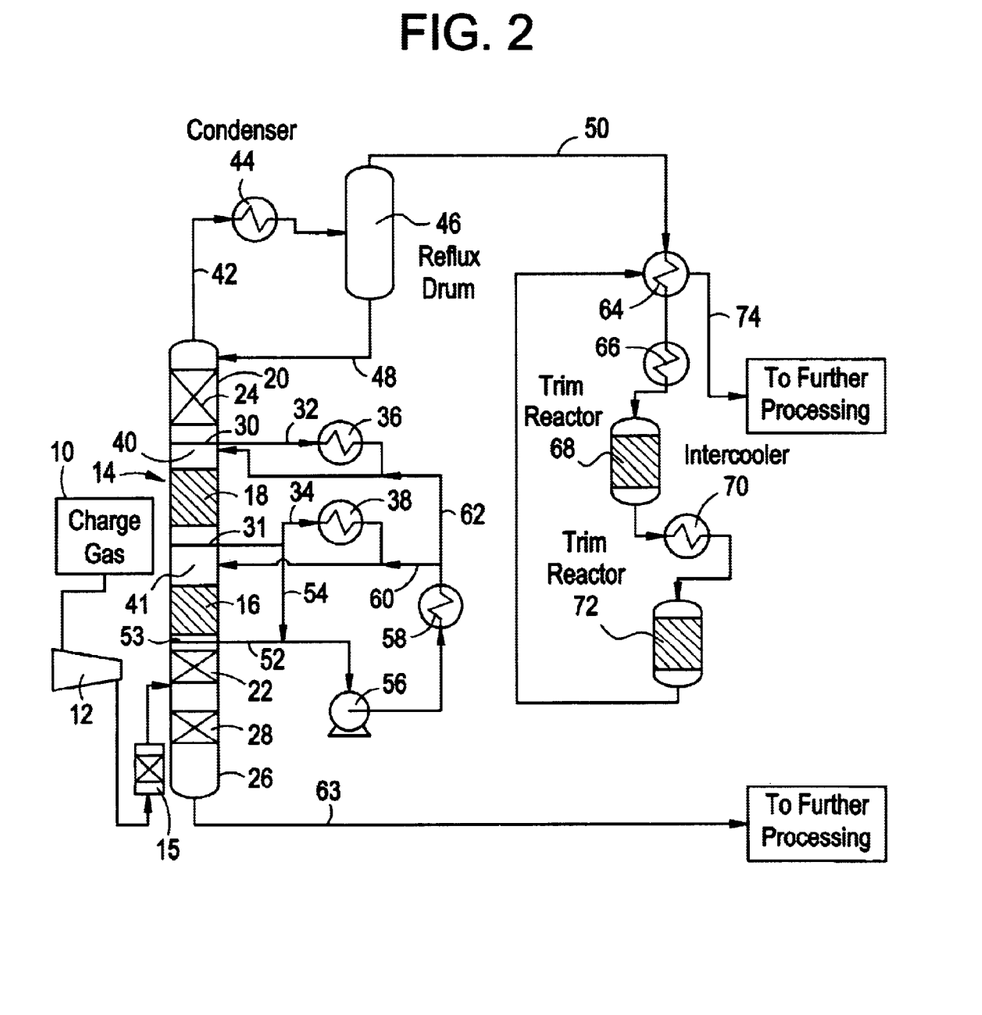
FIG. 2 is a flow diagram illustrating the present invention.

Referring now to FIG. 2 that illustrates one embodiment of the present invention, the charge gas 10 is compressed at 12 to between 150 and 250 psig and then fed to the catalytic distillation column 14. The charge gas may or may not be preheated to match column temperatures. The charge gas would typically pass through one or more guard beds 15 to remove such poisons as lead (Pb), arsenic (As) and mercury (Hg). These are known catalyst poisons and the guard beds would be employed in a known manner to protect the catalytic distillation catalyst. Entering the catalytic distillation column, the 8% to 20% by weight diene and acetylenic feed is hydrogenated in catalyst beds 16 and 18 located in the rectification section 20 of the column. The catalytic beds could be of the same or different catalytic composition. The catalysts are known hydrogenation catalysts consisting primarily of one or more Group VIIIA metals (Ni, Pd, Pt) on a support. Additives such as Ag or Au and/or alkali metals are typically used to control selectivity and activity. Specific examples of selective hydrogenation catalysts particularly suited for this service are disclosed in U.S. Pat. Nos. 6,417,136; 5,587,348; 5,698,752 and 6,127,588. The catalytic systems used within a catalytic distillation column can consist of either a single catalyst, a catalyst with different metal loadings to adjust activity located in different portions of the column, or mixtures of catalysts of different metals located in different portions of the column. The hydrogenation occurs in the liquid phase in catalytic distillation fashion. Although only two reactive catalytic beds 16 and 18 are shown, this is only by way of example and could be any number of beds depending on the requirements of any particular plant or the desire to adjust catalyst activity through the use of more complex catalyst systems. Fractionation internals 22 and 24, which may be trays or packing, are provided in the rectification section 20. Additional fractionation internals could be located between the catalyst beds 16 and 18. The stripping section 26 contains fractionation internals 28.

The overhead 42 from the column is cooled in the overhead condenser 44 with cooling water or with refrigeration as needed and the resulting vapor and liquid are separated in the reflux drum 46. The resulting liquid from reflux drum 46 is fed through line 48 back into the column as reflux. Similar to the prior art, the overhead vapor 50 contains most of the $C_5$ and lighter compounds while the liquid phase 48 is used to reflux the column. The vapor overhead 50 however does not pass into subsequent fractionation but into a fixed bed reactor system consisting of one or more beds of catalyst with provision for heating and/or cooling the vapor feed. Overhead 50 is first exchanged against final fixed bed reactor system effluent 74 to recover heat. It then passes to heater 66 where the temperature of the vapor entering the first fixed bed reactor 68 is controlled. In reactor 68, some portion of the $C_2$ acetylene as well as some portion of the $C_3$ and heavier acetylenes and dienes that were not converted in the catalytic distillation column are hydrogenated. The conditions and the number of fixed bed reactors employed are such that the $C_2$ acetylene is completely removed from effluent stream 74 with no loss of ethylene and propylene over the entire system (catalytic distillation plus fixed bed reactors). The addition of the fixed bed reactor system to the catalytic distillation column dramatically increases both the performance of the entire system and the ability of that system to respond to process variations and catalyst deactivation.

The operating criteria for the rectification section of the catalytic distillation column is that conditions be created wherein the unsaturated hydrocarbons are hydrogenated to the extent possible without any hydrogenation of ethylene and propylene. This is accomplished by:

1. Operating the column such that ethylene and propylene in the liquid phase is minimized, and
2. Operating the catalytic distillation column such that there are still unconverted $C_2$ to $C_5$ acetylenes and diolefins remaining in column overhead 50.

In the catalytic distillation operation of the present invention, the distillation function is designed and operated to distill essentially all of the $C_5$ and lighter components as overhead and essentially all of the $C_6$ and heavier components as bottoms. Alternately, the split could be at the $C_4$ carbon number where essentially all of the $C_4$ and lighter components go overhead and the $C_5$ and heavier components leave as bottoms. In order to selectively hydrogenate the $C_2$ acetylenes, the $C_3$ acetylenes and dienes, and the $C_4$ and heavier acetylenes, dienes and olefins while leaving the ethylene and propylene un-hydrogenated, the rectification section 20 is operated such that there is a substantial concentration gradient of $C_4$ and $C_5$ materials relative to $C_2$ and $C_3$ materials in the liquid phase where the majority of the hydrogenation reaction occurs. This can be controlled by variation of reboiler duty and reflux rate to achieve the desired overhead and bottoms composition.

The choice of operation of the catalytic distillation column as either a depentanizer or a debutanizer will be a function of both the composition of the feed and the desired hydrogenation requirements for the products. The preferred operating conditions for a depentanizer will be a pressure of between 75 and 350 psig and a catalyst bed temperature between 50 and 150 C. Similarly, the preferred operating conditions for a debutanizer column will be a pressure between 100 and 400 psig and a catalyst bed temperature between 30 and 130 C.

In addition to controlling the overall fractionation, the temperature and composition profiles over the reactive sections can be controlled by adjusting the rates of heat removal over the column and by recirculation of liquid within and/or around the catalyst beds. As shown in FIG. 2, trays 30 and 31 collect the descending liquid which is withdrawn as side streams 32 and 34. These streams may or may not pass through the intercoolers 36 and 38 and then be reinjected back into the column through the distribution headers 40. This permits a portion of the heat of reaction to be removed in the intercoolers. By arranging the intercoolers in this fashion, the cooling medium can be water while the cooling in the overhead condensers may need to be at least partly provided by mechanical refrigeration. Hence, the use of the intercoolers can significantly reduce the portion of the heat of reaction which needs to be removed by mechanical refrigeration.

The hydrogenation in the column 14 occurs in the liquid phase. The extent of the reaction is dependent upon the relative reactivity of the various components and the concentration of these components in the liquid phase at any particular point in the column. The $C_2$ and $C_3$ acetylenes and dienes are far more reactive than ethylene and propylene so that they react first and rapidly. However, the relative reactivities of ethylene, propylene and the $C_4$ and heavier olefins, dienes and acetylenes are very close. In order to react a significant quantity of the $C_4$ and heavier olefins, dienes and acetylenes without any significant loss of ethylene and propylene, the concentration of the ethylene and propylene in the liquid phase must be minimized and the concentration and temperature profiles from top to bottom must be controlled. Since this stage of the hydrogenation occurs in a fractionation column, this control can be accomplished by adjusting the overhead reflux produced by the overhead condenser 44 and the side stream reflux from the intercoolers 36 and 38. The liquid compositions of ethylene and propylene can be kept low in the reactive zones through increases in the flow of reflux 48 and/or increased interbed cooling at 36 and 38.

In the catalytic distillation unit 14, the recycle and pumparound circuits have been modified from the prior art as illustrated in FIG. 1. That prior art shows simple intercoolers 180 and an overall pumparound line 260. In the present invention, the system is modified to provide the flexibility to have both uncooled and cooled pumparounds in the catalyst zones 16 and 18 within the rectification section 20. This improvement permits the desired temperature and composition control with minimal disturbance to the overall distillation. This is accomplished by drawing off pumparound liquid immediately below the catalyst beds as stream 52 and/or 54 from withdrawal points 53 and 31 respectively and returning it through the pump 56 and heat exchanger 58 to the top of the same bed as streams 60 and/or 62. Alternatively, the liquid can be drawn from the bottom most catalyst bed and returned to the highest bed via stream 62. Cooling at 58 can be used, if necessary, to provide combined composition adjustment and intercooling between reactive beds. For example, while withdrawal intercooling stream 34 from point 31, cooling that stream in exchanger 38 and returning the flow to distribution system 41 will cool the liquid but not change the composition. However, withdrawing the same liquid from 31, passing it via line 54 through pump 56 to exchanger 58, cooling the liquid and returning it to liquid distributor 40 above the catalyst bed will change the composition profile within the column. This design flexibility can be used to maximize the efficiency of the hydrogenation. In this fashion, the option of cooling against a warmer cooling medium available in the prior art is maintained with the modified pumparound/intercooler reducing the expensive low level cooling required in the overhead system. Further, the heat removed by these pumparound streams can be utilized elsewhere in the ethylene plant to reduce energy consumption. Another advantage of the new pumparound scheme is that it allows for relatively large liquid flow without affecting the overall column separation performance due to heavies in the overhead as in the prior art. With the large liquid flows, the pumparound can provide the necessary liquid loading over the catalyst without the need for additional reflux. This permits operation of the catalytic distillation column at lower reflux ratios than previously possible without the penalty in distillation efficiency observed with the prior art. Reflux ratios in the range of 0.5 to 1.8 by weight are satisfactory for producing the necessary catalyst liquid wetting where values as high as 5 were required with the prior art. In addition to the obvious reduction in energy requirements, higher hydrogen partial pressures due to the lower reflux ratios will be available in the present invention resulting in lower required catalyst volumes.

In a catalytic distillation column, it is critical to keep the catalyst wetted at all times to insure that the reaction occurs in the liquid phase. The selectivity of a catalytic distillation system relies in part on the reaction taking place in the liquid phase while certain components that the operator wishes to remain unreacted such as ethylene remain in the highest concentration in the vapor phase. Maintaining a certain liquid traffic down the column is critical to keeping the catalyst wetted. If the liquid traffic is greater than 800 lb liquid/hr/ft$^3$ of column cross-section, the catalyst will be highly wetted and reaction selectivity will be maintained.

A secondary control variable would be variation in the reflux with associated variation in reboiler duty. In this way, both catalyst bed temperature and composition may be altered to achieve the desired hydrogenation.

Additionally, a variable feed location allowing for a main feed point below the stripping section 22 will provide some separation of any heavy components present in the feed before reaching both the catalyst bed 16 and the side stream 52 for the first pumparound. In this way, circulating the heavy, potentially fouling components over the catalyst bed is eliminated. In addition, feed points above the first catalyst bed can be incorporated to allow for turndown operation and thus avoid the problems of excess catalyst and resultant selectivity loss under these lower flow conditions. The bottoms 63 from the column 14 are sent for further processing as desired.

As shown in FIG. 2, the present invention includes the addition of a fixed bed trim reactor system providing further hydrogenation of stream 50. This system is typically two reactors with an intercooler but could be a series of reactors with intercoolers between successive reactors. The fixed bed reactor system provides four advantages:

1. The catalytic distillation column no longer needs to operate for high levels of hydrogenation but can be operated for the maximum productivity from the catalyst, a net ethylene gain with high acetylene, methyl acetylene, and propadiene conversion while maintaining acetylene $C_2$ specification.
2. Changes in the catalytic distillation overhead concentration of acetylenics and dienes resulting from catalyst deactivation, carbon monoxide content increase, or feedstock change can be accommodated.
3. Hydrogen removal can be maintained during temporary upsets and/or catalyst deactivation or poisoning thus stabilizing performance of downstream refrigeration systems. If the quantity of hydrogen from the system were to vary, the partial pressures of the downstream distillation system would change and the required quantity of refrigeration would vary. This would create process upsets and be very undesirable.
4. Opportunity for catalyst regeneration by the use of spare fixed bed reactors thus extending onstream operating life of the entire system.

In addition to control of the temperature and composition profile over the column, it is important to operate with less than complete conversion of the acetylenes and dienes over the catalytic distillation column. By doing so, ethylene and propylene gains can be achieved. Further, this operation requires less catalyst than the full hydrogenation of the prior art thus maximizing catalytic distillation catalyst productivity. Operation with a fixed bed reactor system following the column allows this to occur.

Figure 3:
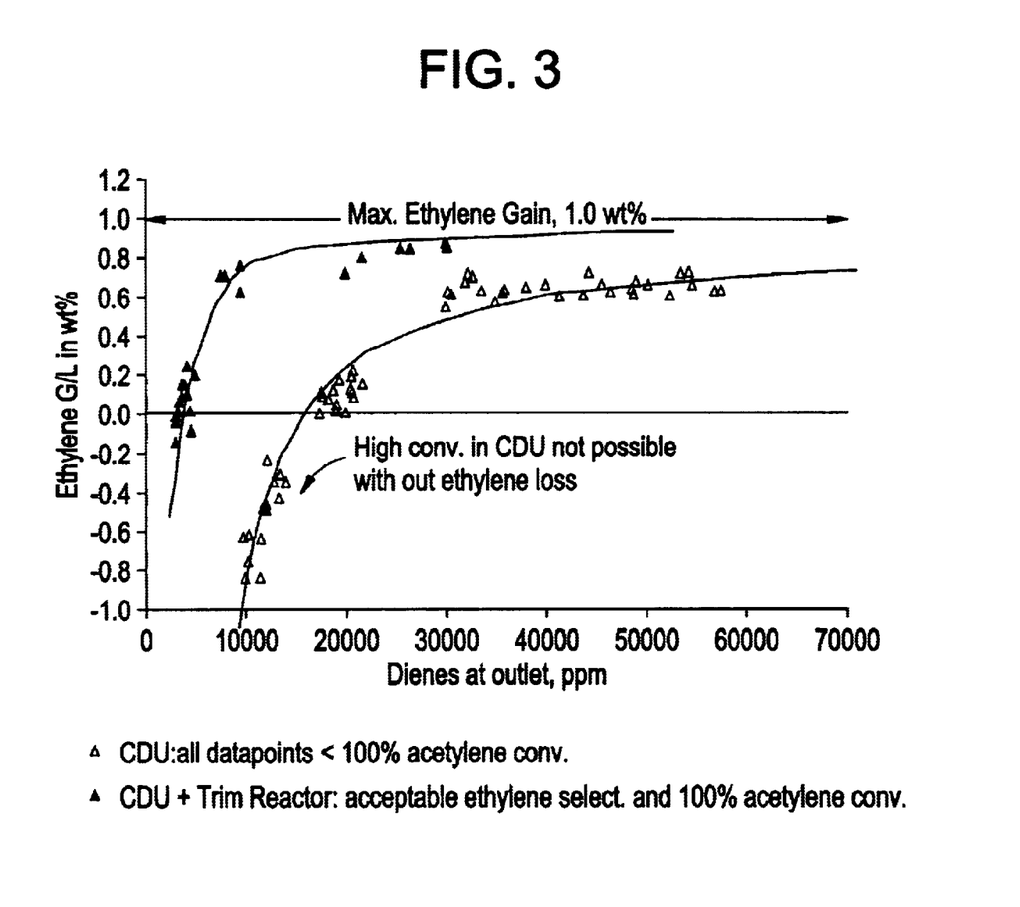
FIG. 3 is a graph illustrating the ethylene gain or loss versus the diene output level for the present invention compared to the prior art.

If the column were to be operated such that there is no more than approximately 1% ethylene liquid concentration in the reactive beds, hydrogenation in excess of 95% of the $C_2$ to $C_5$ and heavier dienes can be achieved. This results in 5000–7500 ppm dienes and acetylenics in the vapor stream 50 from the reflux drum 46 and a minimum ethylene loss of 1%. To make 100% acetylene conversion, ethylene losses would even be higher. This operation coincides to a hydrogen removal of approximately 30–35% depending upon the feed composition. However, when the overall conversions of the $C_2$ to $C_5$ and heavier dienes and acetylenics are reduced to between 80 and 95% resulting in 10,000 to 20,000 and typically 15,000 ppm $C_2$ to $C_5$ diene and acetylene in the outlet stream 50, ethylene gains can be achieved. FIG. 3 is a plot of the dienes at the outlet in ppm versus the ethylene gain or loss in weight percent for a catalytic distillation unit (CDU) alone and for a CDU plus a fixed bed hydrogenation system. As can be seen from FIG. 3, allowing a certain quantity of highly reactive acetylenes and dienes to remain unreacted in the overhead from the catalytic distillation column, ethylene and propylene losses can be eliminated while still obtaining 100% conversion of acetylene overall.

With fixed bed reactors located after the catalytic distillation column 14, $C_2$ acetylene breakthrough with 10,000 to 55,000 and typically 20,000 ppm combined $C_3$ and heavier dienes and acetylenes can be tolerated from the catalytic distillation column. A typical system with two fixed bed hydrogenation reactors with intercooling has been shown to hydrogenate 100% of the $C_2$ acetylenes entering the fixed bed reactor system and approximately 75% of the combined $C_3$ and heavier dienes and acetylenes entering the fixed bed reactor system. This results in 2500 to 14,000 and typically only 5000 ppm breakthrough of dienes and acetylenics from the combined system. This represents approximately 97% hydrogenation of the total $C_2$ and heavier acetylenes and diolefins in the feed. Such operation allows for substantial overall ethylene gains of up to 0.5% with 70% overall acetylene selectivity toward ethylene at 100% acetylene conversion. This is a substantial improvement over the prior art.

The specific hydrogenation reactivity of ethylene is just slightly lower than the specific reactivity of propadiene. Thus close observation of the $C_3$ diene conversion provides a reliable indication of the stability of the ethylene gain and can be used as a control point for the system. For the catalytic distillation system alone, when $C_3$ diene conversion is between 40 and 60% and typically 45%, ethylene losses are observed. However, when operating at conditions where the $C_3$ diene conversion in the catalytic distillation column is between 10 and 35% and typically 20%, ethylene gains from 0.2% to 0.5% are possible. With the present invention, the propadiene conversion can be increased substantially while still maintaining ethylene gain.

During the normal operation of an ethylene unit, variations in the carbon monoxide content of charge gas 10 is experienced. In addition, feedstock quality or operating severity may be changed that will impact the acetylenic and diolefin content of charge gas. For a fixed catalyst volume in the catalytic distillation column, increases in carbon monoxide or inlet diene and acetylenic concentrations result in lower conversion and thus higher releases of these undesired products into stream 50. Compensation for such anticipated disturbances would be difficult with the prior art alone as shown in FIG. 1. It would require increases in operating pressure or temperature impacting the performance of the entire fractionation system. In the improved process including a fixed bed reactor system, the temperature of the vapor 50 entering the fixed bed reactor system can be adjusted to either increase or decrease reactivity of the reactor system and thus follow changes in catalytic distillation reaction activity and maintain complete $C_2$ acetylene removal and high hydrogen removal efficiency.

Finally, a fixed bed hydrogenation reactor system is designed to include not only operating reactors but also spares. Catalyst deactivation will occur in both the fixed bed system and the catalytic distillation system. It is not possible to regenerate the catalytic distillation catalyst without shutting down the process or installing a parallel column. Both options are costly. However, a spare fixed bed vapor phase reactor is a relatively inexpensive option. By utilizing a fixed bed reactor system with a spare instead of the single column concept of the prior art, onstream life of the process can be substantially improved.

In the fixed bed hydrogenation system, the net overhead 50 from the catalytic distillation passes through the cross flow heat exchanger 64 and inlet heater 66 into the first fixed bed reactor 68. The effluent from the first reactor 68 goes through the intercooler 70 to the second fixed bed hydrogenation in reactor 72. A series of fixed beds followed by intercoolers can be used in the same fashion in order to achieve the necessary heat transfer when required. The effluent from the last reactor 72 then goes back through the cross flow heat exchanger 64 where heat is extracted and the feed 50 to the fixed bed reactors is heated. The inlet temperature to the fixed bed reactors can be quickly changed to either increase or decrease the extent of hydrogenation in the fixed bed reactors. Such control is necessary to successfully handle changes in carbon monoxide or diene and acetylene feed concentration. Up to a maximum adiabatic temperature rise of 80° F. total for both beds, a stable fixed bed operation with no ethylene loss is possible. A typical adiabatic rise of 35° F. is expected for normal operation. With an adiabatic temperature rise of 70 to 80 and typically 80° F., handling of 35000 to 58000 and typically 43000 ppm acetylenes and dienes from the catalytic distillation results in 9000 to 30000 and typically 10000 ppm $C_3$ and heavier dienes and acetylenics in the final product stream 74 while maintaining 100% $C_2$ acetylene conversion primarily to ethylene.

In a similar fashion, the temperature control on the inlet to the fixed bed reactors can provide for compensation for catalyst deactivation providing the typical start-of-run and end-of-run operating temperatures to the fixed bed system. In the prior art, this could only be done by a temperature correction in the catalytic distillation column. This requires a pressure change in the column and thus the fractionation conditions will be altered. With both the catalytic distillation column and fixed bed reactor system of the present invention the catalytic distillation column can operate at constant fractionation conditions and lower temperature corrections for the fixed bed system will be required. This improves system stability and allows for longer life of the catalyst.

Figure 4:
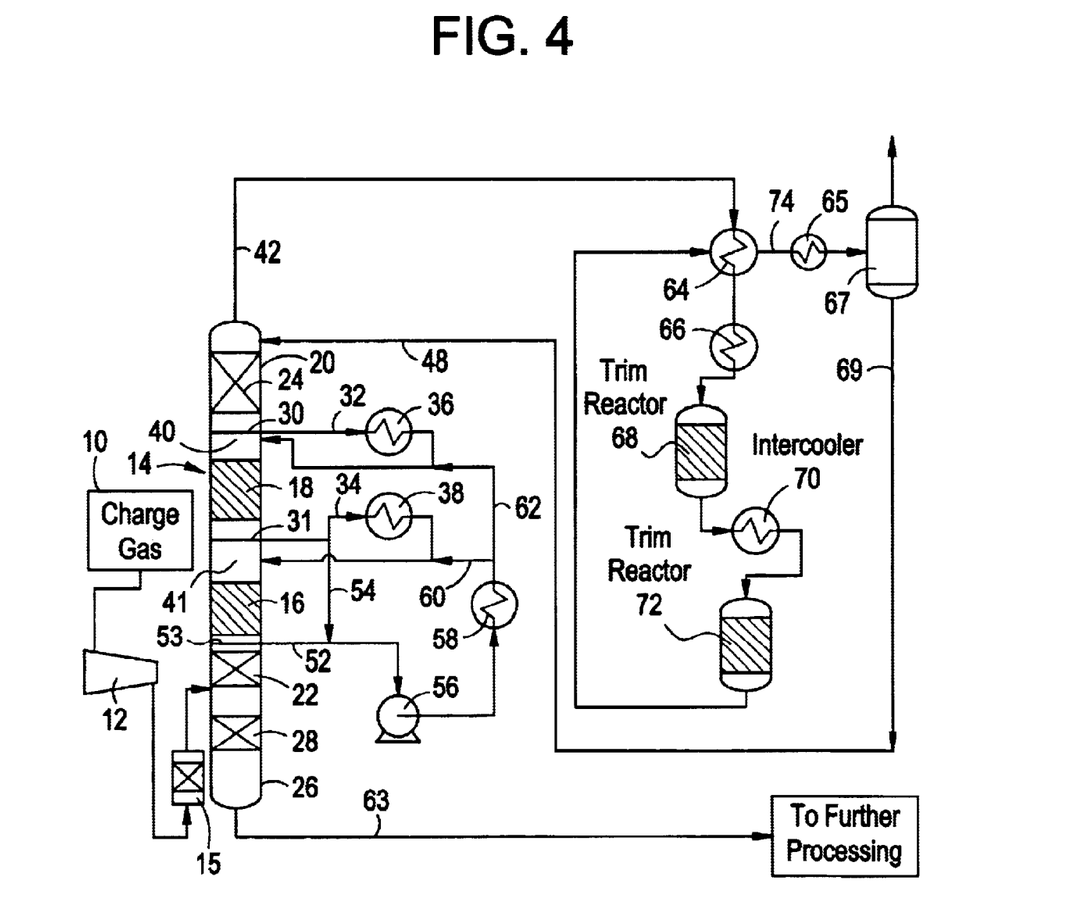
FIG. 4 is a flow diagram similar to FIG. 2 but illustrating another embodiment of the present invention.

FIG. 4 presents an alternate embodiment of the present invention. Instead of catalytic distillation column overhead stream 42 passing to exchanger 44 and then to reflux drum 44, overhead stream 42 is passed directly to cross-flow exchanger 64 and into the fixed bed reactor system. Following the fixed bed reactor system, the effluent is cooled at 65 and the reflux 48 for the column is separated at 67 as a condensed liquid 69 and returned to the column.

Since the stream entering the fixed bed reactor system still contains all of the reflux for the column, the operating temperature of the fixed bed reactors will be somewhat higher to insure complete vapor flow. This will change the design catalyst activity and space velocity to insure stable operation. The advantage of this approach will be a higher mass flow of hydrocarbon that will minimize temperature rise across the fixed beds, a reduced hydrogen partial pressure that will improve selectivity, and a higher space velocity that will both improve selectivity and decrease catalyst costs.

Figure 5:
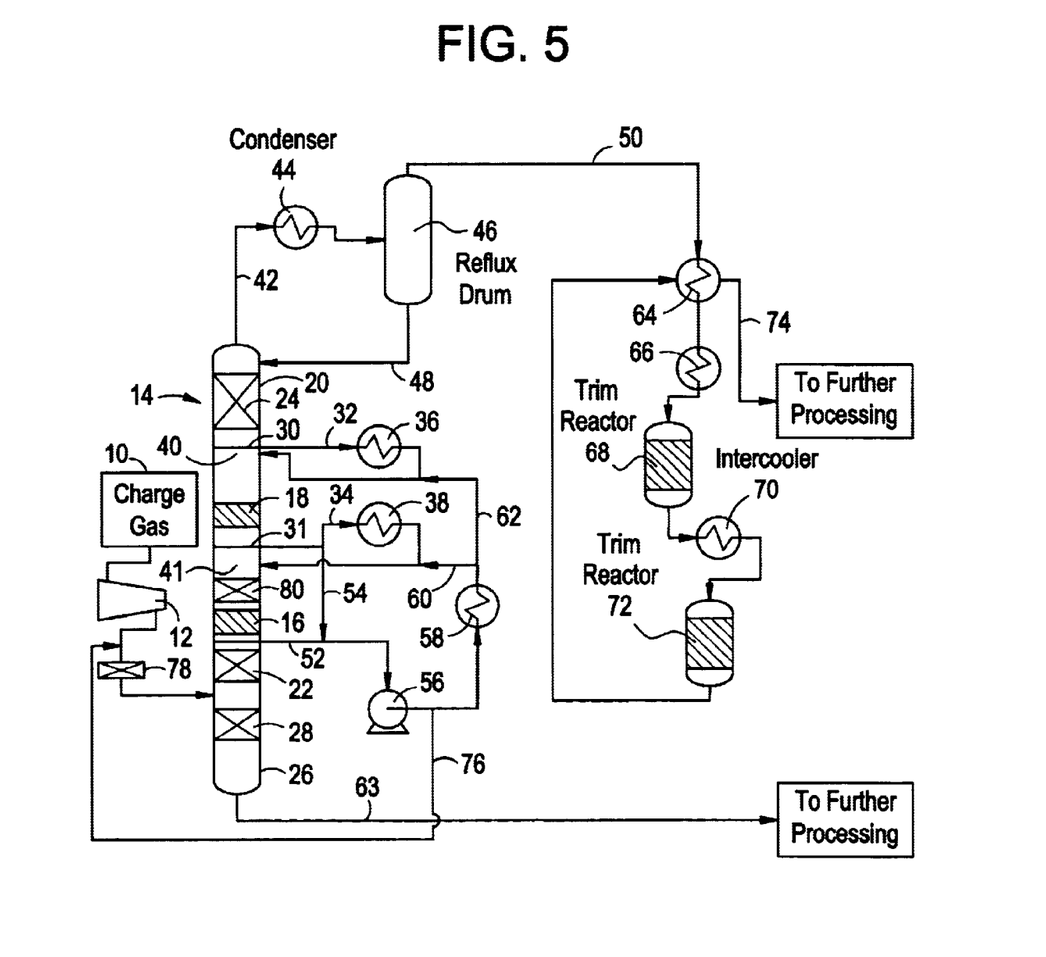
FIG. 5 is a flow diagram of an alternate embodiment of the present invention.

FIG. 5 illustrates an alternate embodiment of the present invention incorporating a pre-reactor. This arrangement is advantageous for bulk selective hydrogenation of feeds high in dienes and acetylenes. Following compression at 12 and possible treatment in a guard bed (not shown), the vapor phase feedstock is admixed with recirculation liquid 76 from the pump 56 of column 14 and the two phase mixture passed co-currently through a fixed bed reactor 78. Hydrogenation occurs and the presence of liquid serves to control the temperature rise through vaporization. Hydrogenation reactor 78 can be designed as an operating reactor plus a spare to allow for extending the onstream operation of the system. Following the pre-reactor, the liquid/vapor mixture can be either sent to the column directly as a mixed feed or separated in a separation drum and the liquid and vapor fed separately to the column. The latter is preferred since any oligomers formed in the initial hydrogenation will be in the liquid phase and can be fed to the column below the catalyst beds thus reducing fouling.

Performing the fixed bed hydrogenations before the catalytic distillation column 14 will allow for possibly higher catalyst utilization without experiencing ethylene loss for that portion of the hydrogenation due to the large amount of preferentially absorbed dienes and acetylenes of higher reactivity available for hydrogenation. At higher catalyst utilization, lower catalyst volumes would be necessary making the process more economical. A catalytic distillation unit is still required following a pre-reactor to reach hydrogenation specifications. It is anticipated that a maximum of 50% and typically 20% of the hydrogenation duty can be accomplished in the pre-reactor.

Another advantage of a fixed bed hydrogenation reactor before the catalytic distillation column 14 is that the reactor can be used as a guard bed for catalyst poisons. The catalyst could either be nickel or palladium. Nickel catalyst for example would be able to catalyze the reaction of the sulfur compound thiophene with butadiene to form a heavy mercaptan. This mercaptan would then be removed in the stripping section 22 of column 14 and thus never contact the palladium catalyst. A still further advantage is that the external pre-reactor system could have a spare and thus allow for regeneration without the requirement for shutting the entire plant down for catalyst replacement.

Figure 6:
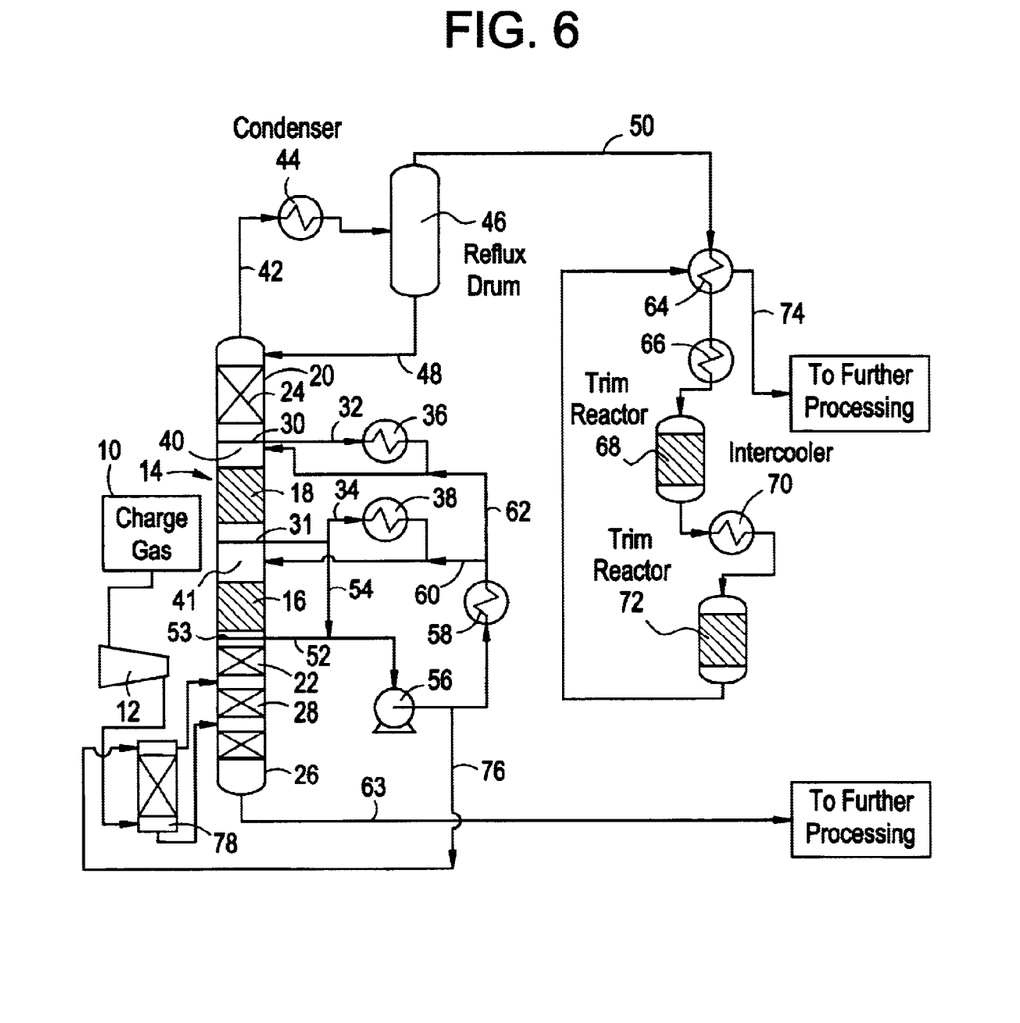
FIG. 6 is a flow diagram illustrating an alternate embodiment of the process of FIG. 5.

Alternately, as shown in FIG. 6, the liquid 76 from pump 56 can flow downwards through the fixed bed 78 and the vapor stream from the compressor 12 can flow upwards. Liquid from the bottom of the fixed bed reactor 78 then flows to a lower portion of column 14 and vapor flows to a higher entry point. The advantage of this counter-current process sequence is that oligomers resulting from polymerization reactions of the unsaturated hydrocarbons are removed from the catalyst bed as formed and do not pass over the remaining portion of the catalyst bed. Also this liquid is sent to column 26 at a lower entry point, minimizing any potential contamination of the catalyst in column 14.

Oligomers which can foul the catalytic distillation catalyst are easily separated and do not rise in the column to contaminate the catalyst. Further, as in the co-current flow option, the pre-reactor catalyst bed can have a spare, allowing for regeneration while the rest of the system is operating. The ability to easily regenerate on-line will increase system cycle lengths as the catalyst zone at the feed inlet is expected to have the highest fouling rate.

To minimize fouling in the fixed bed pre-reactor, liquid flow rates need to be sufficient to minimize local hot spots due to the high heat of hydrogenation and to wash any oligomers formed off the catalyst. The operation of these beds is preferably in the vapor continuous zone. For cracked gas feeds that exhibit extreme fouling tendencies, operating in the liquid continuous zone is also possible.

Figure 7:
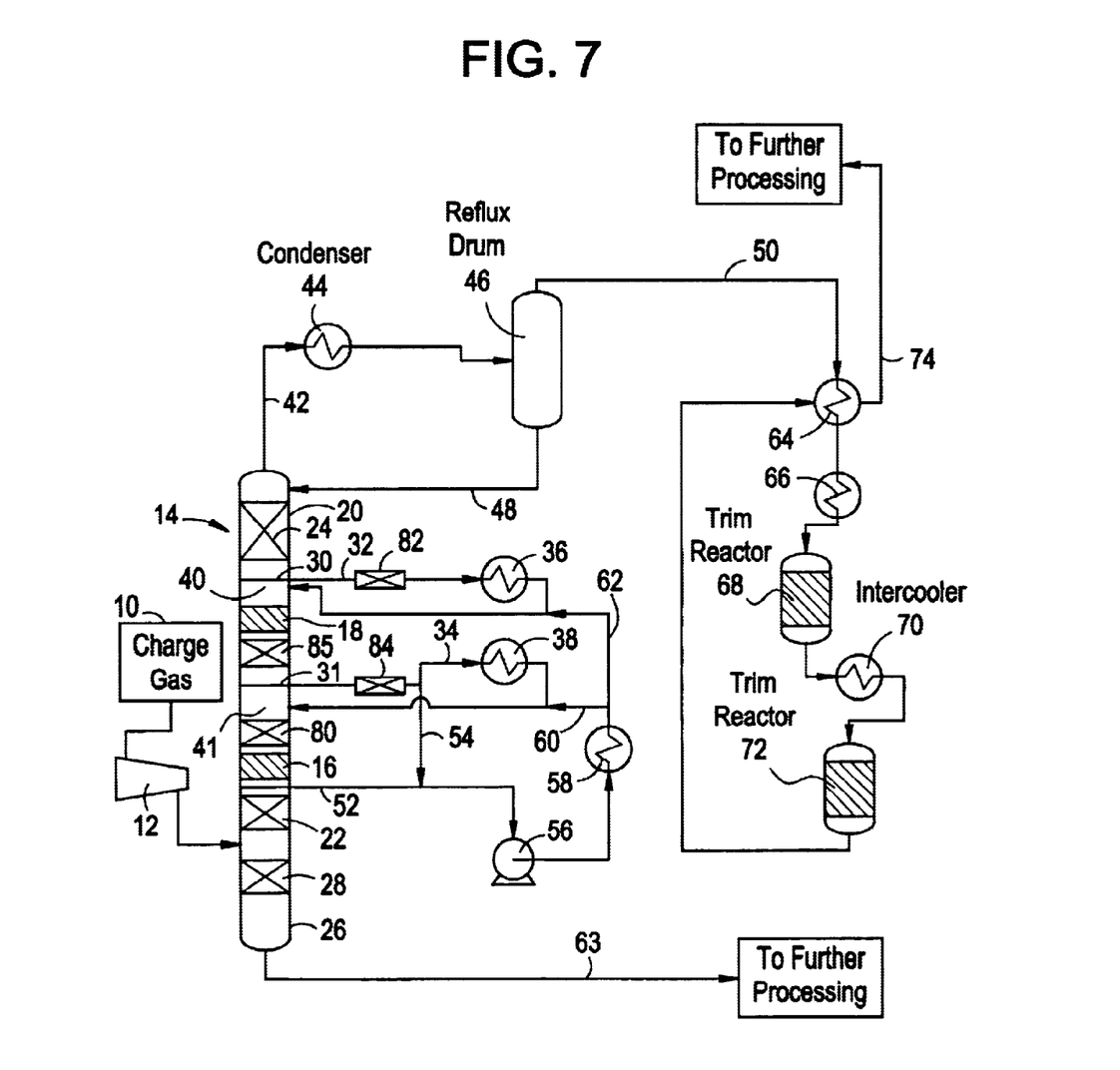
FIG. 7 is a flow diagram similar to FIG. 2 but illustrating an alternate embodiment of the present invention.

FIG. 7 illustrates a further embodiment of the present invention which incorporates fixed bed reactors within the liquid pumparound or intercooler streams that are withdrawn from the column 14. The fixed bed hydrogenation reactors 82 and 84 are placed in the side stream from collecting tray 30 and the side stream from collecting tray 31, respectively. These fixed beds 82 and 84 are in addition to the reactive hydrogenation sections 16 and 18 in the hydrogenation sections 16 and 18 in the catalytic distillation column 14. A mass transfer zone 85 in the form of structured packing or trays is also added above the withdrawal point and below the catalyst bed. This zone allows for hydrogen to be saturated into the liquid phase and thus provide the hydrogen required for the hydrogenation of the acetylenes and dienes in the withdrawn liquid.

The ability of the present invention to remove 30 to 40% of the hydrogen from the charge gas prior to chilling and condensation steps lowers the energy consumption and reduces capital cost. The ability to hydrogenate 100% of the acetylene irrespective of the carbon monoxide concentration without any $C_2$ or $C_3$ olefin losses was not possible with the prior art. The combined fixed bed and catalytic distillation steps provide superior handling of system upsets while maintaining stable diene/acetylene hydrogenation and hydrogen removal.

Following are some examples which illustrate the present invention in its various embodiments as compared to the prior art. The following Table 1 sets forth the feed composition used for all the examples. Table 2 lists the results for each of the examples.

TABLE 1

| Component | wt % |
|---|---|
| Hydrogen | 1.07 |
| Lights | 18.22 |

TABLE 1-continued

| Component | wt % |
|---|---|
| Total C2 | 24.21 |
| C2 acetylene | 0.22 |
| Total C3 | 25.62 |
| C3 diene and acetylenics | 1.70 |
| Total C4 | 13.96 |
| C4 dienes | 5.27 |
| Total C5 | 4.83 |
| C5 diene | 2.10 |
| C6+ | 12.09 |

TABLE 2

| | Example 1 | Example 2 | Example 3 | Example 4 | Example 5 |
|---|---|---|---|---|---|
| Column P (psig) | 195 | 195 | 195 | 195 | 195 |
| Average Catalyst T (° F.) | 230 | 232 | 228 | 231 | 228 |
| CO/H2 ratio (mol %) | 0.3 | 0.3 | 0.6 | 0.3 | 0.6 |
| Catalyst Utilization (lbmole H2/ft3/hr) | 0.12 | 0.13 | 0.09 | 0.12 | 0.09 |
| Fixed Bed Inlet T (° F.) | — | — | — | 129 | 140 |
| Fixed Bed GHSV | — | — | — | 1800 | 2000 |
| Conversions (%) | | | | | |
| C2 acetylene | 84 | 89 | 80 | 100 | 100 |
| H2 conversions | 28 | 30 | 20 | 34 | 31 |
| C2 ethylene gain/loss | 0 | (0.6) loss | 0.6 | 0.1 | 0.7 |
| C3 propylene gain/loss | 4.7 | 5.1 | 3.4 | 5.8 | 4.8 |
| C4 olefin conversion | 0.7 | 0.8 | 0.4 | 2.0 | 1.8 |
| Ppm outlet (wt) Total | 19070 | 12340 | 33860 | 3640 | 7740 |
| C2 acetylene | 370 | 240 | 460 | 0 | 0 |
| C3 acetylene | 2300 | 1600 | 3900 | 300 | 840 |
| C3 diene | 3400 | 2900 | 4500 | 2900 | 4000 |
| C4 diene | 11500 | 7000 | 21700 | 150 | 1500 |
| C5 diene | 1500 | 600 | 3300 | 290 | 1400 |

EXAMPLE 1

This example represents prior art outlined in the previous U.S. Pat. No. 5,679,241 (FIG. 1) based on a one step catalytic distillation column operating with a reflux ratio of 4.4. With a typical front end acetylene hydrogenation catalyst containing palladium levels below 2000 ppm and operating at pressure of 195 psig and average catalyst temperature of 230° F. $C_2$ acetylene conversion reached 84% with 0% ethylene loss/gain. At the reactor outlet there were 370 ppm of $C_2$ acetylene and a total of 19070 ppm dienes and acetylenics. Total acetylene/diene conversion is 79.5%. This example represents the case where the single column is operated for no ethylene loss. As can be seen, there is substantial breakthrough of $C_2$ acetylene. This would produce off-spec ethylene product.

EXAMPLE 2

This example also represents prior art and is based on the single catalytic distillation column of Example 1 with higher catalyst temperature and slightly lower reflux ratio of 4.1. The hydrogenation severity of a single column can be increased to reach low $C_2$ acetylene levels. This can be accomplished by raising temperature or increasing catalyst activity. The higher temperature operation is intended to reduce acetylene content and thus achieve specification ethylene product. In this case all the diene and acetylenic conversions are higher compared to Example 1, however there is also a 0.6% ethylene loss. At the reactor outlet there were 240 ppm of $C_2$ acetylene and a total of 12340 ppm dienes and acetylenics. Total acetylene/diene conversion is 86.7%. As can be seen, increased $C_2$ acetylene conversion is accompanied by increased ethylene loss that is economically undesirable. Further, the ethylene product still does not meet the specification limits of 1–2 ppm.

EXAMPLE 3

This example represents prior art and is based on the single catalytic distillation column of Example 1 with higher carbon monoxide levels in the feed. Carbon monoxide acts as a catalyst poison and therefore diene and acetylenic conversions were substantially reduced. At carbon monoxide levels of 0.1 mol % in the feed (0.6% carbon monoxide to hydrogen ratio) the product had 460 ppm of acetylene and 33860 ppm of total dienes and acetylenics. The lower catalyst activity resulting from the CO is reflected on the loss of catalyst productivity (0.12 to 0.09 lbmol/hr-ft3 catalyst structure) and the lower overall acetylene/diene conversion (63.6% versus 79.5% for the base case).

The response to this reduced activity would be to raise the temperature of the catalyst within the catalytic distillation column. This would require an increase in pressure beyond what is practical in an operating unit. Thus options to compensate for CO increases are limited for the prior art.

EXAMPLE 4

This example represents the improved combined operation of the catalytic distillation column and a fixed bed reactor described in FIG. 2. This combined operation is necessary in order to realize ethylene gains with 100% $C_2$ acetylene conversion and 50% to 95% conversion of all other diene and acetylene compounds. Operation of the catalytic distillation column at 195 psig and average catalyst temperature of 230° F. and 195 psig pressure resulted in 12,000 ppm by weight dienes and acetylenes in the catalytic distillation overhead which was then fed to the fixed bed hydrogenation reactor system.

Operation of the fixed bed hydrogenation reactors at gas hourly space velocity (GHSV) of 1800 $h^{-1}$ and inlet bed temperatures of 129° F. was successful in converting 100% of the $C_2$ acetylene and provide enough additional hydrogenation resulting in 50% overall $C_3$ diene conversion (both catalytic and fixed bed hydrogenation), as well as 96.1% overall conversion of the dienes and acetylenes in the feed to the combined system. This resulted in 0 ppm of $C_2$ acetylene and 3640 ppm $C_3$ and heavier diene and acetylenes in the outlet. Specification ethylene product can be produced with very high overall conversion of the highly unsaturated species.

EXAMPLE 5

This example represents the improved combined operation of the catalytic distillation column and a fixed bed reactor at high carbon monoxide levels in the feed. At carbon monoxide levels of 0.1 mol % in the feed with constant operating conditions for the catalytic distillation column, only the fixed bed inlet temperature needed to be adjusted in order to maintain product specifications. Specifically, with an increase in carbon monoxide from 0.05 to 0.1 mol %, an increase in the inlet fixed bed temperature from 129 to 140° F. was sufficient to maintain the conversion of the $C_2$ acetylene. Further, the $C_3$ and heavier dienes and acetylenes were further hydrogenated resulting in 7740 ppm wt. total diene and acetylenes in the product.

The proposed improvement of the present invention will perform 100% $C_2$ acetylene hydrogenation with stable 90%+hydrogenation of the $C_3$ to $C_5$ and heavier acetylenes, 90%+hydrogenation of $C_4$ and $C_5$ dienes, and 50%+ conversion of $C_3$ diene in a feed stream without hydrogenating the $C_2$ and $C_3$ olefins. The resulting hydrogen removal with the present invention will remain steady at 30 to 40 and typically 30% depending on the feed composition.

What is claimed is:

1. A method of processing a thermally cracked feed stream containing hydrogen, ethylene, propylene, acetylene, methyl acetylene, propadiene and other $C_4$, $C_5$, $C_6$ and heavier unsaturated hydrocarbons to hydrogenate and convert essentially all of said acetylene in high proportion to ethylene and hydrogenate at least a portion of the methyl acetylene, propadiene and other $C_4$, $C_5$, $C_6$ and heavier unsaturated hydrocarbons to olefins and to thereby consume a portion of said hydrogen without hydrogenating ethylene and propylene comprising the steps of:
   a. introducing said feed stream into a catalytic distillation column containing at least one hydrogenation catalyst bed and concurrently:
      (i) selectively hydrogenating a portion of said acetylene to form ethylene and hydrogenating portions of said methyl acetylene, propadiene and $C_4$, $C_5$, $C_6$ and heavier unsaturated hydrocarbons and controlling the hydrogenation conditions whereby said ethylene and propylene are not hydrogenated; and
      (ii) separating by fractional distillation said feed stream into lighter hydrocarbons and heavier hydrocarbons;
   b. removing substantially all of the remaining portion of said hydrogen and said lighter hydrocarbons as a vapor phase overhead and substantially all of said heavier hydrocarbons as bottoms from said catalytic distillation column;
   c. introducing at least a portion of said vapor phase overhead into a vapor phase fixed bed reactor system containing a hydrogenation catalyst and hydrogenating the remaining portion of said acetylene to form further ethylene and hydrogenating further portions of said methyl acetylene, propadiene and $C_4$, $C_5$, $C_6$ and heavier unsaturated hydrocarbons and controlling the hydrogenation conditions whereby said ethylene and propylene are not hydrogenated; and
   d. removing mixed product from said fixed bed reactor system.

2. A method of claim 1 where said lighter hydrocarbon consists of $C_4$ and lighter hydrocarbons and said heavy hydrocarbon consists of $C_5$ and heavier hydrocarbons.

3. A method of claim 1 where said lighter hydrocarbon consists of $C_5$ and lighter hydrocarbons and said heavy hydrocarbon consists of $C_6$ and heavier hydrocarbons.

4. A method as recited in claim 1 and further comprising the steps of condensing a portion of said vapor phase overhead and returning said condensed portion to said catalytic distillation column as reflux.

5. A method as recited in claim 1 wherein essentially all of said vapor phase overhead is introduced into said vapor phase fixed bed reactor system and further comprising the step of returning a portion of said product from said fixed bed reactor system to said catalytic distillation column as reflux.

6. A method as recited in claim 1 wherein said step of controlling said step of selectively hydrogenating in said catalytic distillation column and in said vapor phase fixed bed reactor includes the steps of controlling the temperature profile therein.

7. A method as recited in claim 6 wherein said step of controlling the temperature profile in said catalytic distillation column includes the step of withdrawing a portion of liquid descending in said column at a selected point as a sidestream, cooling said sidestream and injecting said cooled sidestream back into said column at or above said selected point.

8. A method as recited in claim 7 and further including the step of hydrogenating said sidestream.

9. A method as recited in claim 6 wherein said step of controlling the temperature profile in said catalytic distillation column includes the step of withdrawing a pumparound stream from a point in said column below said hydrogenation catalyst beds, cooling said pumparound stream and injecting said cooled pumparound stream back into said column above said hydrogenation catalyst beds.

10. A method as recited in claim 1 wherein said vapor phase fixed bed reactor system comprises at least one reactor and wherein said step of controlling the temperature therein comprises the step of controlling the temperature in heat exchangers prior to said reactor.

11. A method as recited in claim 1 wherein said vapor phase fixed bed reactor system comprises two or more reactors in series and wherein said step of controlling the temperature therein comprises the steps of controlling the temperature in heat exchangers prior to each of said reactors.

12. A method of claim 1 where said step of selectively hydrogenating consists of the step of operating said catalytic distillation column such that the concentration of ethylene in the liquid phase in the catalyst bed is less than 2% by weight.

13. A method of claim 1 where said step of selectively hydrogenating consists of the step of operating said catalytic distillation column such that the liquid flow down the column is greater than 800 lb/hr/ft$^2$ of cross-sectional area in the area of the catalyst bed.

14. A method as recited in claim 1 wherein said step of introducing said feed stream into said catalytic distillation column includes the step of mixing said feed stream with a recycle liquid from said catalytic distillation column and introducing said mixed feed stream and recycle liquid into a fixed bed hydrogenation pre-reactor prior to said catalytic distillation column whereby a portion of the highly unsaturated hydrocarbons is hydrogenated and the vapor and liquid streams are introduced into said catalytic distillation column.

15. A method as recited in claim 1 wherein said hydrogenation catalyst bed in said catalytic distillation column contains a catalyst consisting of a group VIIIA metal on a support.

16. A method as recited in claim 12 wherein said catalyst comprises palladium on alumina.

17. A method as recited in claim 13 wherein said catalyst also includes an additive selected from the group consisting of gold, silver and alkali metals.

18. A method as recited in claim 14 wherein catalysts having different quantities of palladium thereon are located in selected portions of said catalytic distillation column.

19. A method as recited in claim 15 wherein different catalysts are located in different portions of said catalytic distillation column.

20. A method as recited in claim 19 wherein said different catalysts contain different metals.

21. A method as recited in claim 19 wherein said different catalysts have different metal loadings.

22. A method as recited in claim 15 wherein said catalyst comprises nickel on a support.

23. A method as recited in claim 15 wherein said catalyst comprises a combination of palladium on a support and nickel on a support in different portions of said catalytic distillation column.

24. A method as recited in claim 1 wherein said hydrogenation catalyst in said fixed bed reactor system comprises a group VIIIA metal on a support.

25. A method as recited in claim 24 wherein said hydrogenation catalyst in said fixed bed reactor system comprises palladium on alumina.

26. A method as recited in claim 24 wherein said hydrogenation catalyst in said fixed bed reactor system comprises palladium on alumina with a promoter consisting of gold, silver, an alkali metal or combinations.

27. A method as recited in claim 14 wherein said fixed bed hydrogenation pre-reactor contains a nickel catalyst and said pre- reactor causes the reaction of sulfur compounds for removal.

28. A method as recited in claim 1 and further comprising the step of removing catalyst poisons from said feed stream prior to the introduction into said catalytic distillation column.

29. A method as recited in claim 28 wherein said catalyst poisons are lead, arsenic and mercury.

* * * * *